United States Patent

Maget et al.

[11] Patent Number: 5,971,722
[45] Date of Patent: Oct. 26, 1999

[54] ELECTROCHEMICAL SYRINGE PUMP HAVING A SEALED STORAGE RESERVOIR FOR A CHARGE TRANSFER MEDIUM

[75] Inventors: Henri J. R. Maget, La Jolla; Robert Rosati, Carlsbad; Lisa Davis, San Diego, all of Calif.

[73] Assignee: Baxter International Inc, Deerfield, Ill.

[21] Appl. No.: 08/924,564

[22] Filed: Sep. 5, 1997

[51] Int. Cl.[6] ............................ F04B 35/02; F04B 35/04
[52] U.S. Cl. .......................... 417/379; 204/301; 604/140
[58] Field of Search ................................. 204/228, 265, 204/266, 252; 429/54; 604/140, 134, 143; 417/379, 472, 473

[56] References Cited

U.S. PATENT DOCUMENTS

| | | | |
|---|---|---|---|
| 4,402,817 | 9/1983 | Maget | 204/301 |
| 4,522,698 | 6/1985 | Maget | 204/301 |
| 4,556,612 | 12/1985 | Thibault et al. | 429/54 |
| 4,592,753 | 6/1986 | Panoz | 604/897 |
| 4,648,955 | 3/1987 | Maget | 204/258 |
| 4,687,423 | 8/1987 | Maget et al. | 417/379 |
| 4,822,617 | 4/1989 | Panoz | 424/449 |
| 4,886,514 | 12/1989 | Maget . | |
| 4,902,278 | 2/1990 | Maget et al. | 604/132 |
| 4,969,874 | 11/1990 | Michel et al. | 604/140 |
| 4,973,469 | 11/1990 | Mulligan et al. | 424/461 |
| 5,038,821 | 8/1991 | Maget | 137/486 |
| 5,135,480 | 8/1992 | Bannon et al. | 604/20 |
| 5,149,413 | 9/1992 | Maget | 204/258 |
| 5,186,805 | 2/1993 | Gross et al. | 204/265 |
| 5,242,565 | 9/1993 | Winsel | 204/265 |
| 5,334,304 | 8/1994 | Maget | 204/421 |
| 5,417,822 | 5/1995 | Maget | 204/153.18 |
| 5,454,922 | 10/1995 | Joshi et al. | 204/265 |
| 5,527,288 | 6/1996 | Gross et al. | 604/140 |
| 5,533,995 | 7/1996 | Corish | 604/870.1 |
| 5,538,605 | 7/1996 | Joshi et al. | 204/266 |
| 5,567,287 | 10/1996 | Joshi et al. | 204/265 |
| 5,593,552 | 1/1997 | Joshi et al. | 204/228 |
| 5,744,014 | 4/1998 | Gordon et al. | 204/266 |
| 5,779,677 | 7/1998 | Frezza | 604/134 |
| 5,810,778 | 9/1998 | Hjertman | 604/143 |

*Primary Examiner*—Charles G. Freay
*Assistant Examiner*—Robert Z. Enora
*Attorney, Agent, or Firm*—Francis C. Kowalik

[57] ABSTRACT

An electrochemically driven syringe pump for infusion of medicament wherein the pump has a detachable barrel in which medicament can be stored and subsequently infused. The pump is further adapted for storage as the charge transfer medium is sealed in a reservoir prior to activation.

16 Claims, 14 Drawing Sheets

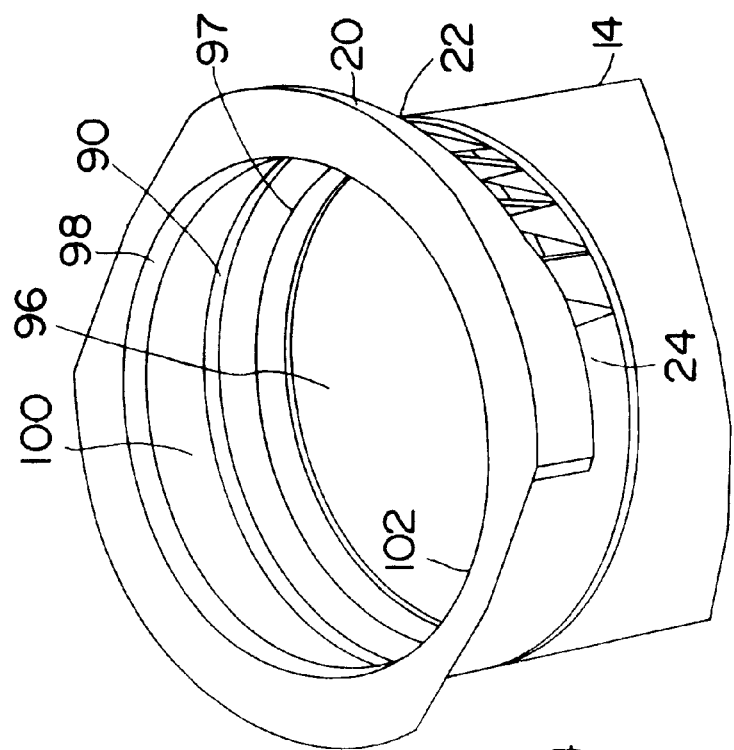
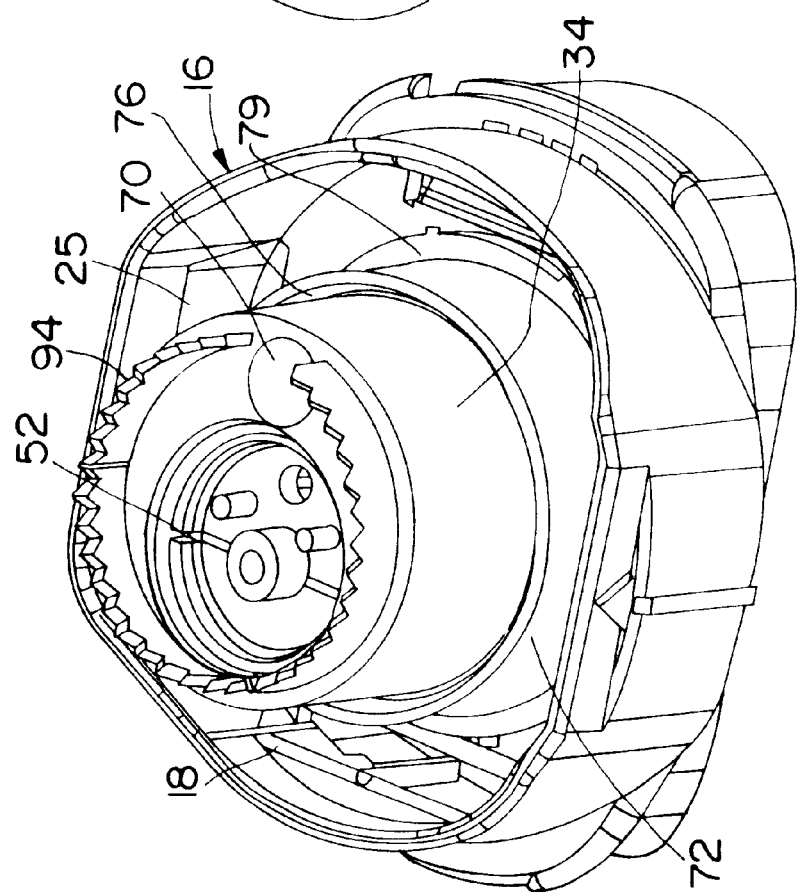
FIG. 12b
FIG. 12a

ELECTROCHEMICAL SYRINGE PUMP HAVING A SEALED STORAGE RESERVOIR FOR A CHARGE TRANSFER MEDIUM

FIELD OF THE INVENTION

The present invention relates to medical infusion devices for parenteral delivery of fluids and more specifically to medical infusion pumps.

BACKGROUND OF THE INVENTION

The medical infusion pump art is one of great breadth and diversity. Even within the art of syringe pumps a great deal of work has been done.

Syringe pumps generally are used to infuse a relatively small quantity of concentrated medicament as opposed to large volume pumps which are designed to infuse accurately a medicament which is formed in admixture with a large quantity of diluent.

Syringe pumps run the gamut from highly accurate and correspondingly expensive electro mechanical pumps such as the Baxter AS40 and other devices from various manufacturers to very inexpensive and correspondingly less accurate disposables; an example thereof being the Disetronic Infusor, which is a galvanic cell, generating Hydrogen, attached to a syringe. Another example of a disposable infusion device is the SmartDoseII™ by River Medical Inc. This device uses an acid-base reaction to produce gas operative to collapse a bag of medicament.

As can be seen by a review of the disposable syringe pump art, of which the above are exemplary, disposable syringe pumps, particularly gas driven syringe pumps, lack the requisite accuracy to deliver many of the latest and most efficacious drugs, particularly drugs for oncology treatments and antibiotics and the like.

The instant invention provides for a level of accuracy similar to that of an electromechanical syringe pump whilst maintaining the simplicity and low cost associated with disposable devices. This accuracy is achieved by use of an accurately current-controlled electrochemical cell which preferentially transfers oxygen out of the air into a specially designed syringe having an essentially constant coefficient of friction throughout the length thereof against the syringe plunger.

An additional shortcoming of gas driven infusion devices is that as the drive gas is being generated there is a delay in infusion at the desired flow rate as the gas pressure rises. In the instant device, the syringe is prepressurized so as to minimize this lead time.

The electrochemistry of electrically driven cells is well characterized. The instant device preferentially uses a cell made of Nafion® from E.I. DuPont de Nemours & Co. Nafion is an acidic material which provides for the reaction:

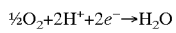

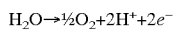

which serves to fill the syringe with oxygen gas. As can be seen from the above reaction, the water is not consumed but rather is recycled as the reaction continues. The water necessary for proton transport when the cell becomes excessively dehydrated is contained in the pump in a novel blotter arrangement which shall be subsequently described.

The combination of the novel electrochemical cell, blotter and prepressurized syringe as well as other aspects of the invention, which shall be subsequently described, provides for an accurate and cost effective pump.

SUMMARY AND OBJECTS OF THE INVENTION

It is a primary object of the invention to provide for a syringe pump having greatly improved accuracy in the delivery of medicaments.

It is another object of the invention to reduce the lead time inherent in gas driven pumps.

It is a third object of the invention to provide a compact and self-contained syringe driving apparatus.

It is a fourth object of the invention to provide for a syringe having an essentially constant coefficient of sliding friction along the throw thereof.

It is a fifth object of the invention to provide for simultaneous assembly and activation of the pump.

It is a sixth object of the invention to provide for an electrochemical cell having a minimized current density gradient across the surface thereof.

It is a seventh object of the invention to provide for an escape valve for excess gas within the syringe.

It is an eighth object of the invention to provide an accurate current controller to an electrochemical cell in an infusion pump.

It is a ninth object of the invention to provide for a sealing ring associated with the plunger of the syringe adapted to provide an essentially constant sliding coefficient of friction.

It is a tenth object of the invention to provide for a syringe that can be prefilled, attached to a pump and subsequently activated.

It is an eleventh object of the invention to provide for an integral assembly operative to supply a source of water to an electrochemical cell.

It is a twelfth object of the invention to provide for an electrochemical pump which is storable for an extended period without loss of efficacy.

It is a thirteenth object of the invention to provide for an improved structure of an electrochemical cell.

These and other objects of the instant invention will become apparent upon review of the claims, specification and drawings appended hereto.

BRIEF DESCRIPTION OF THE DRAWINGS

FIGS. 12a and 12b are perspective views of the syringeward side of the pump head and the distal end of the syringe.

DETAILED DESCRIPTION OF THE PREFERRED EMBODIMENT

Figure 1:
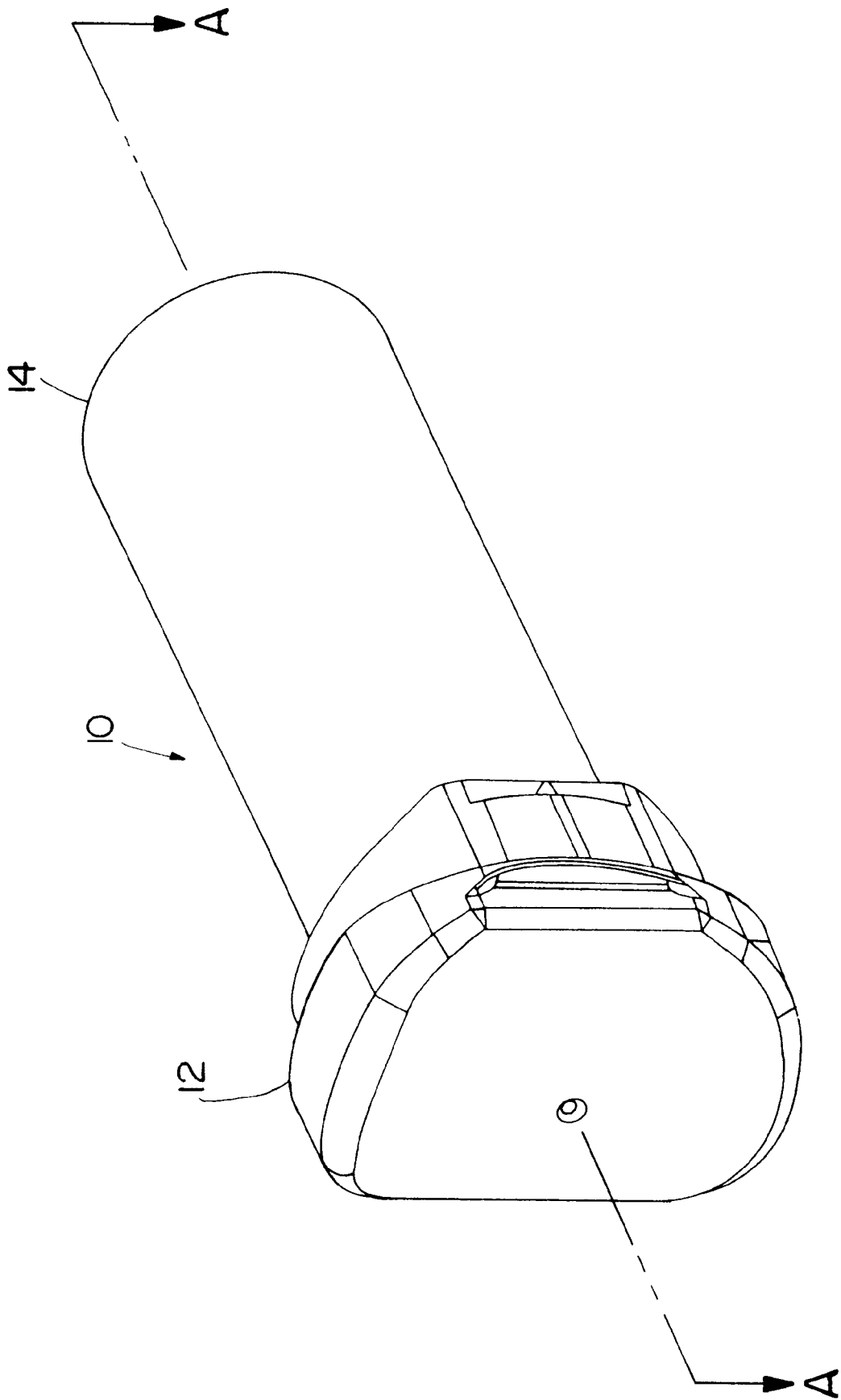
FIG. 1 is a perspective view of the instant invention with the pump head assembled to the syringe.
Figure 6:
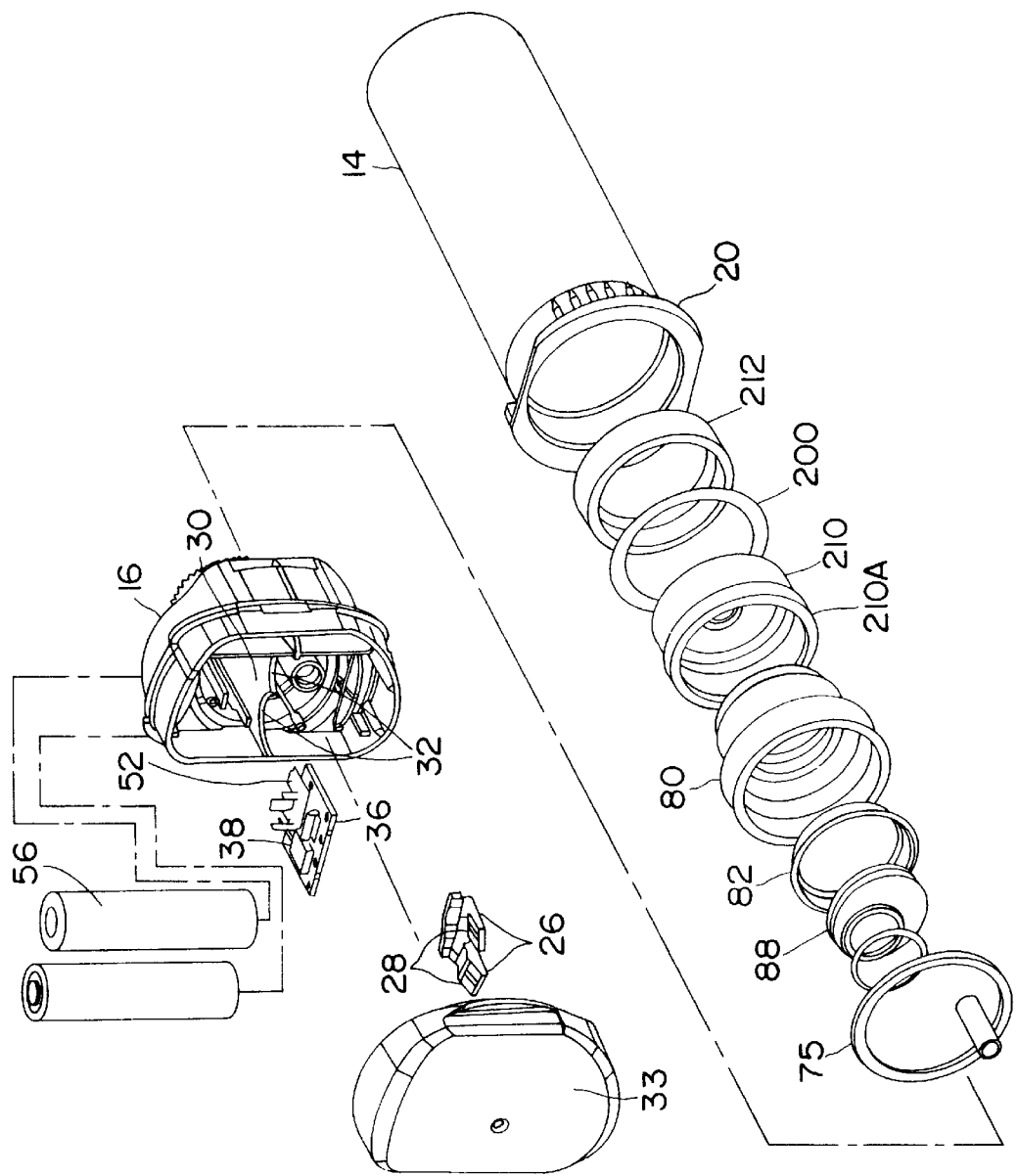
FIG. 6 is an exploded view of the instant invention.

As shown in FIGS. 1 and 6 the preferred embodiment of the instant invention consists of a pump assembly 10 which can be subdivided into a pump module 12 and a syringe body 14. The pump module 12 further consists of a pump housing 16 which is operative to contain the various sub-assemblies of the pump module 12. As shown in FIGS. 12a and 12b, housing 16 defines a peripheral lip 18 which is operative to engage a radially extensive cam 20 associated with the syringe body 14. Peripheral cam 20 defines a first stop position corresponding to a first cam flat 22 which serves to allow the syringe body 14 to be connected to the pump module 12 without activating the pump assembly 10. In the docked but unactivated position, cam flat 22 is engaged with indent 25 so as to allow for the syringe 14 to be engaged with housing 16 without activating the pump. The peripheral cam 20 also defines a second ramp 24, at which point the syringe body 14 is fully engaged with the pump module 12 at which time second ramp 24 has lifted syringe 12 into place so as to allow cam flat 22 to be engaged with lip 18.

Figure 2:
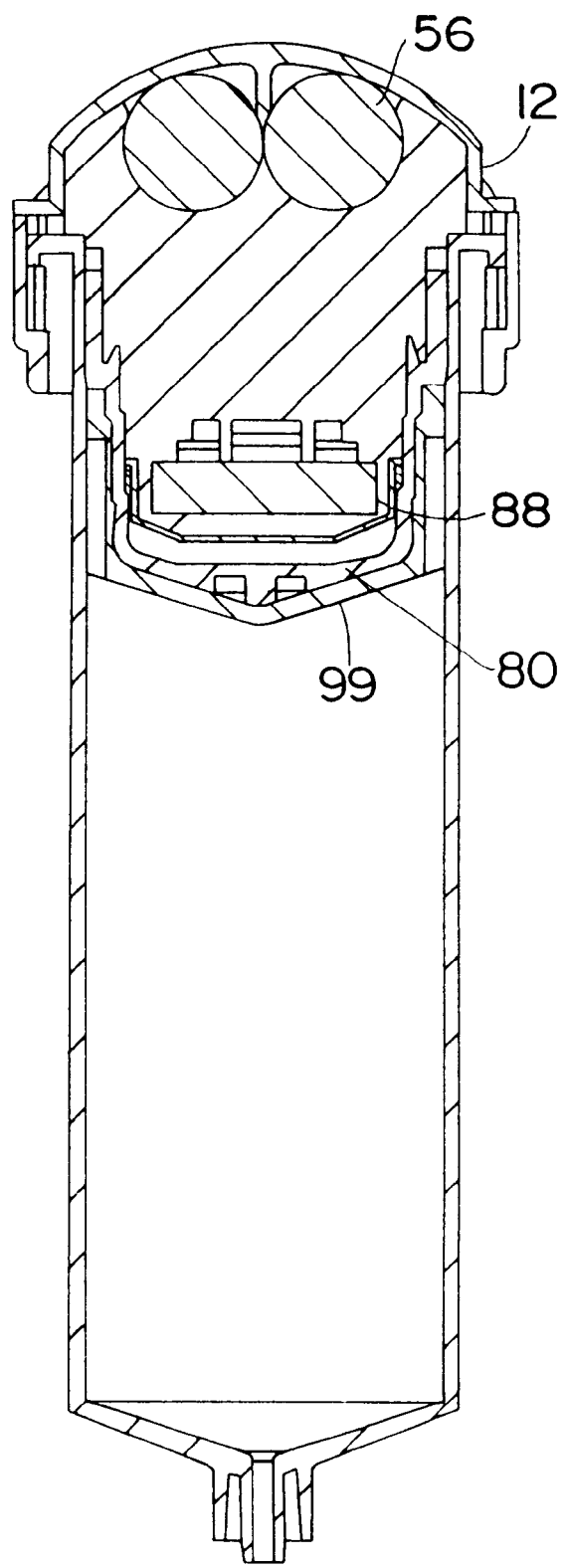
FIG. 2 is a cross-sectional view substantially along line A—A of FIG. 1.

As best seen in FIG. 2, syringe barrel 14 has associated therewith an aft aperture 96 which is adapted to receive a plunger assembly 99. Immediately forward of the aft aperture is a first radial angle 98, shown in FIGS. 12a and 12b, having a height and radial angle defined thereon. Moving forward is annular wall 100 and an annular ramp 90 which is operative to reduce the interior dimension of the syringe barrel 14 to its nominal dimension.

Forward of annular ramp 90 is stop 97 which is operative with plunger assembly 99 to define the syringe volume as well as to retain plunger assembly 99 in syringe barrel 14. The remainder of the syringe barrel being essentially cylindrical and defining an essentially zero draft angle wherein the draft angle is defined as the angle between an axis parallel to the longitudinal axis of the syringe barrel and the wall of the syringe barrel. This minimization of draft angle being operative to provide, in combination with the cruciform sealing ring 200, shown in FIG. 9, which shall subsequently be described, an essentially constant co-efficient of sliding friction between the plunger 210 and the syringe barrel interior 102. Foremost in the syringe is a centrally located output aperture 104 which is adapted to be attached in the preferred embodiment to a luer-type fitting 106 wherein the attachment is operative to connect the syringe to an output tube set so as to deliver medicament to the patient. Returning to the aft or distal end of the syringe annular wall 100 is cooperative with translatable gasket 75 associated with extension 34 so as to provide for a reduction in volume in the gas receiving chamber 110 which is defined within the volume of the syringe barrel 14, the gas receiving chamber being an area within the syringe barrel 14 which is abaft the syringe plunger 210 and sealing ring 200. Translatable gasket 75 is operative to move down the annular wall 100, and by such movement provide for a reduction in volume within the gas receiving chamber 110 so as to cause an increase in pressure in the atmosphere contained therein and is thereby operative to prepressurize the syringe 14 and thereby reduce the lead time before achieving the desired flow rate. This reduction in volume corresponds to the linear translation of the syringe between a first position corresponding to locating cam flat 22 within indent 25 and a second position corresponding to the cam flat 22 engaged with lip 18, shown in FIGS. 12a and 12b, as aforedescribed and being defined as the initial volume of the gas receiving chamber as defined previously and a final volume which is reduced by the difference in position between the first position and the second position.

In operation the syringe body 14 would be attached to the pump module 12 and rotated into the position corresponding to the first cam flat 22 being engaged with indent 25; wherein the filled syringe would remain in such position until time for actual activation by a patient. At this time the syringe body 14 would be rotated relative to the pump module 12 thereby causing the radial extension 18 to engage the first cam flat 22. At this time the radial stop 97 associated with the syringe body 14 would engage cup 80, shown in FIG. 10, and effect the linear translation of the cup as aforedescribed. Simultaneously, translatable gasket or o-ring seal 75, shown in FIG. 6, would move down annular wall 100 thereby reducing the volume of the gas receiving chamber 110 and increasing the pressure therein. Simultaneous thereto, the toothed perforating member 60, best seen in FIG. 11, would puncture the perforatable seal or cover 86 and release the charge transfer medium from the reservoir 82 and affect a transfer of such medium through the charge transfer medium transfer blotter 88 to the electrochemical cell 54.

As seen in FIGS. 12a and 12b, the aft edge of the syringe body 14 includes an aperture 96 wherein the aperture 96 defined by syringe body 14 further defines a first radial angle associated therewith, wherein the first radial angle 98 is operative to provide an initial seat for translatable gasket or o-ring 75. Afore the fist radial angle 98 is the annular wall 100 and a second diameter reducing annular ramp 90 is operative to reduce the syringe body diameter to a final dimension operative to provide a sliding mate with syringe plunger assembly 99.

Figure 5:
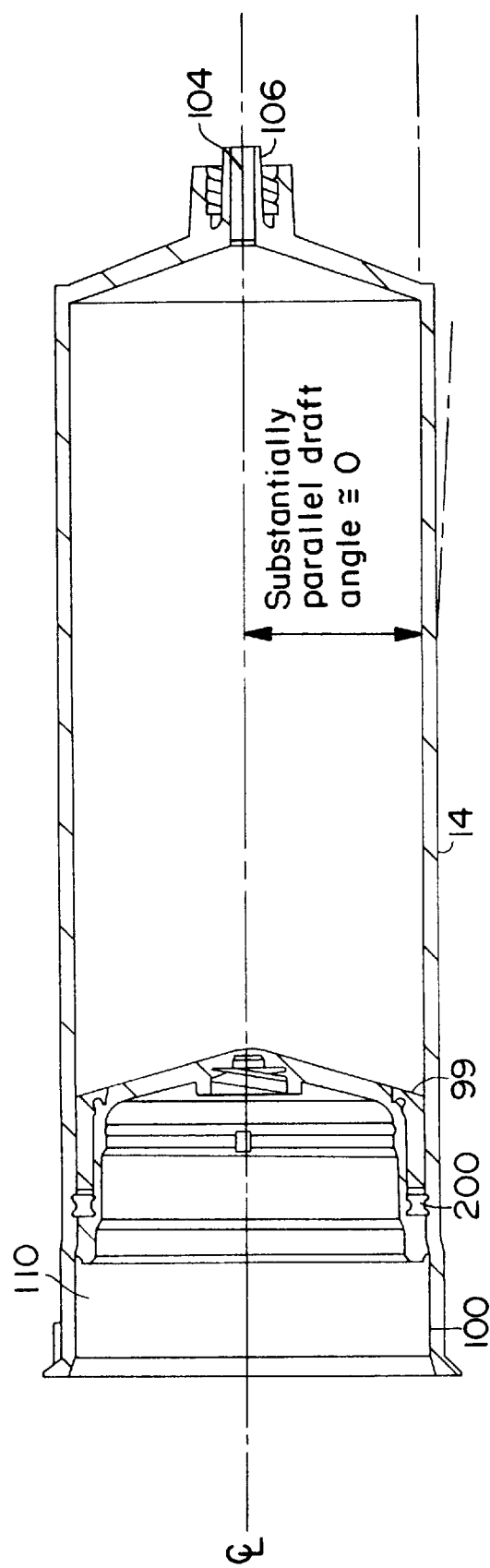
FIG. 5 is a cross-sectional view of the syringe and plunger substantially along the line A—A of FIG. 1.
Figure 9:
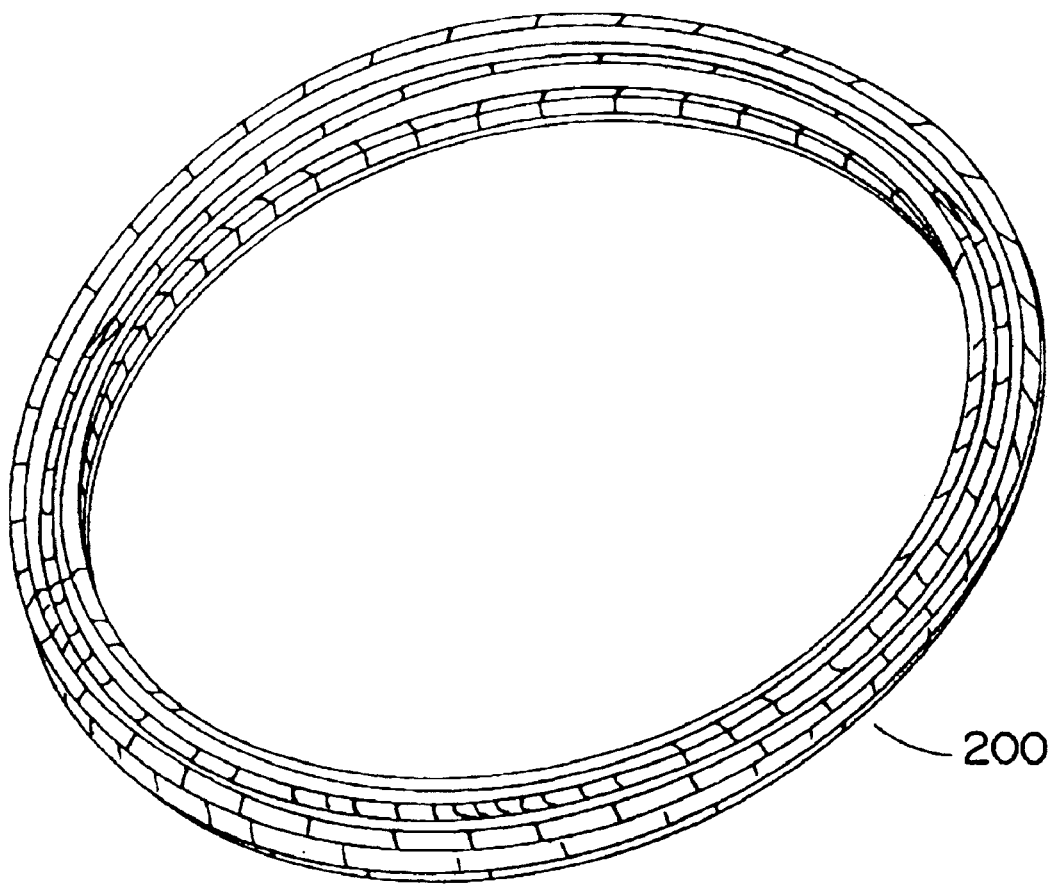
FIG. 9 is a perspective view of the cruciform sealing ring
Figure 14:
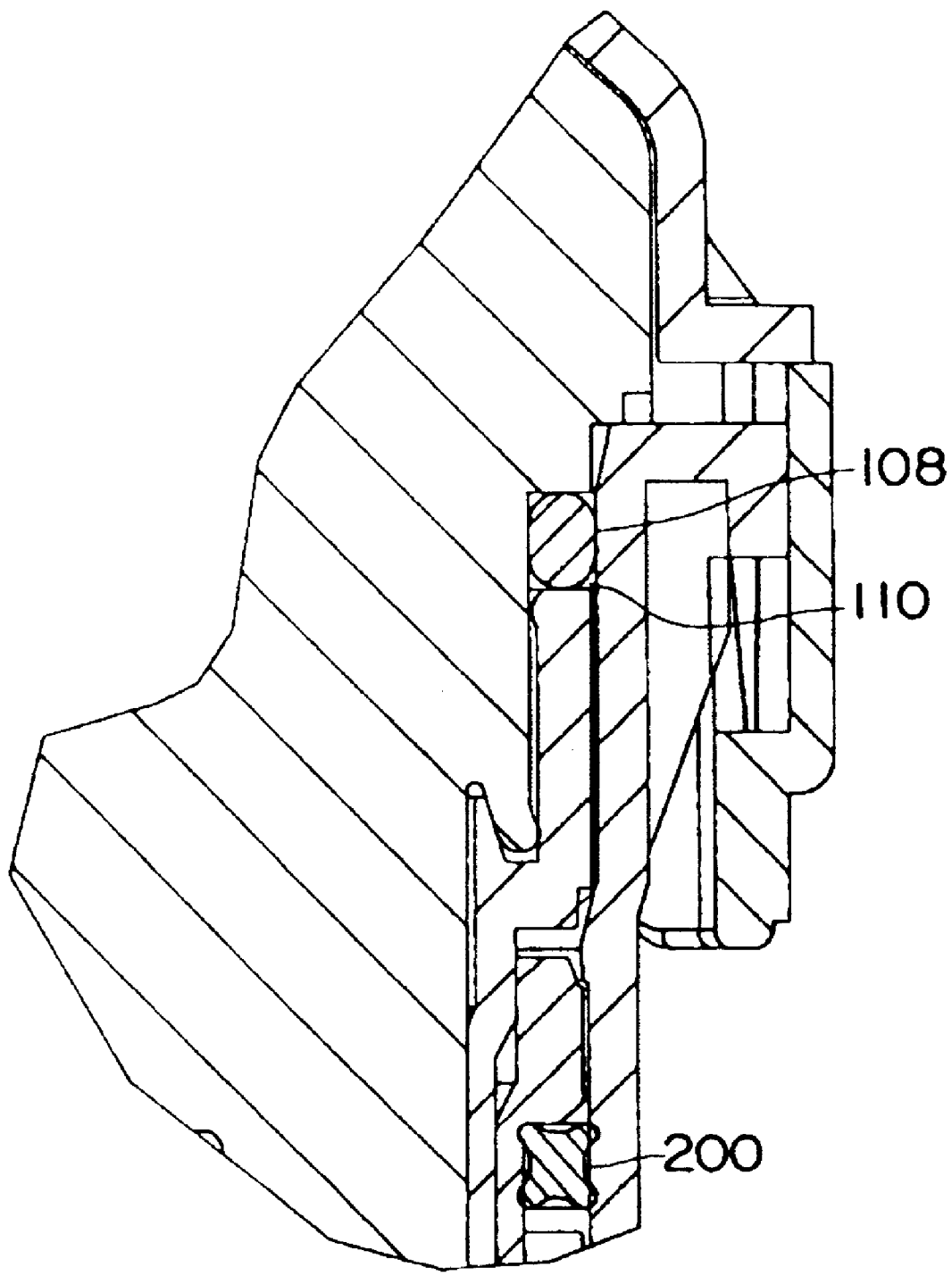
FIG. 14 is a detailed cross-sectional view substantially along the line A—A showing the prepressunrzation means.

As shown in FIGS. 2 and 6, syringe plunger assembly 99 displays a two piece construction wherein the aft plunger body 210 is substantially a stepped cylinder defining an aft extension operative to eliminate tilt of the plunger body 210 within the syringe barrel 14. Mounted on plunger body 210 is a forward cylindrical retaining ring 212 wherein the ring 212 has a slightly smaller external radial dimension than the aft section 210A of the syringe plunger body 210. Best seen in FIG. 5, located in the interstice between the cylindrical retaining member 212 and the aft extension of the syringe plunger 210A is a sliding plunger seal 200. Sliding plunger seal 200 displays a cruciform cross-section as seen in FIGS. 5 and 9 and in cross section FIG. 14, wherein this cross-section is designed to provide for an essentially constant sliding coefficient of friction between plunger assembly 99 and syringe barrel interior 102.

Pump housing 16 further defines a substantially centrally located longitudinal web 30 which has defined thereon a plurality of battery supporting indents 32 and further serves to stiffen housing 16. Additionally associated with housing 16 is a lid 33 and coaxial extension 34 which serves to support the majority of the components associated with housing 16. Nested within the coaxial extension 34 is a printed circuit board 36 which supports current control circuitry 38. The output of this circuitry 38 is transferred via electrode 52 to the electrochemical cell housing 54 which shall be subsequently described. Spring contacts 28 serve to connect batteries 56 electrically to circuit board 36.

Figure 8:
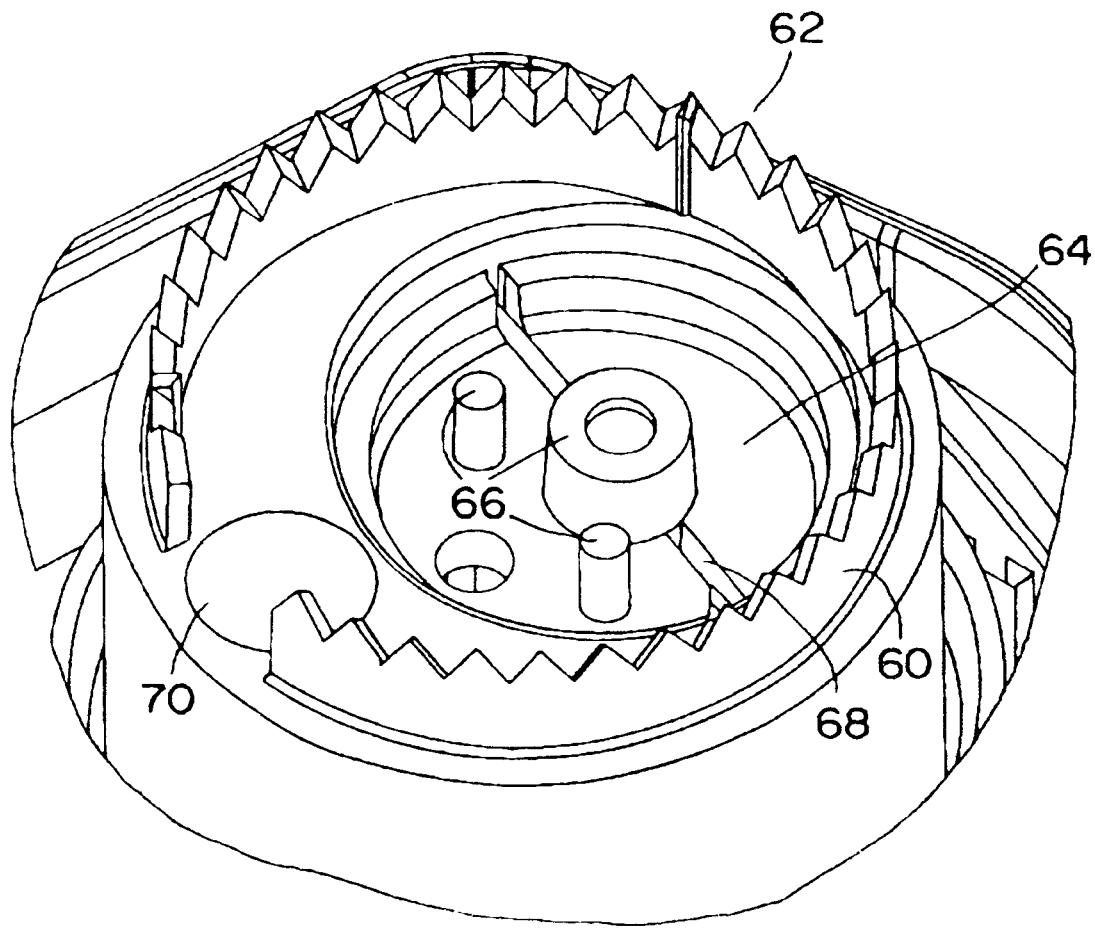
FIG. 8 is a perspective view of the bottom of the pump assembly detailing the sub-assembly associated with the blotter assembly of FIG. 7.

Turning now to FIG. 8, the bottom of housing 16 is shown. Associated with the base of coaxial extension 34 is a toothed perforating member 60 which consists of a plurality of longitudinally extensive teeth 62. Located interior to perforating member 60 is a cell housing supporting indent 64 which has associated therewith support posts 66 which are operative to support the interior surface of the electrochemical cell housing 54. Also associated with indent 64 is feed through port 68 which is adapted to allow spring contact 52 to come into contact with housing 54.

Exterior to indent 64 and parallel therewith housing 16 has defined therein a gas relief valve port 70 which serves to support and contain the overpressure relief valve 300 as shall be subsequently described. Relief valve port 70 is axially extensive to the top of extension 34.

Returning to FIGS. 12a and 12b, extension 34 further defines a radial step 72 which is cooperative with the reservoir cap 80 to retain the cap 80 in a plurality of specific positions which shall be subsequently described. Additionally associated with extension 34 is coaxial groove 76 which is adapted to receive a corresponding coaxial rim 78.

Located uppermost on extension 34 is a sealing ring engaging surface 79 which is adapted to receive sealing ring 75.

Figure 7:
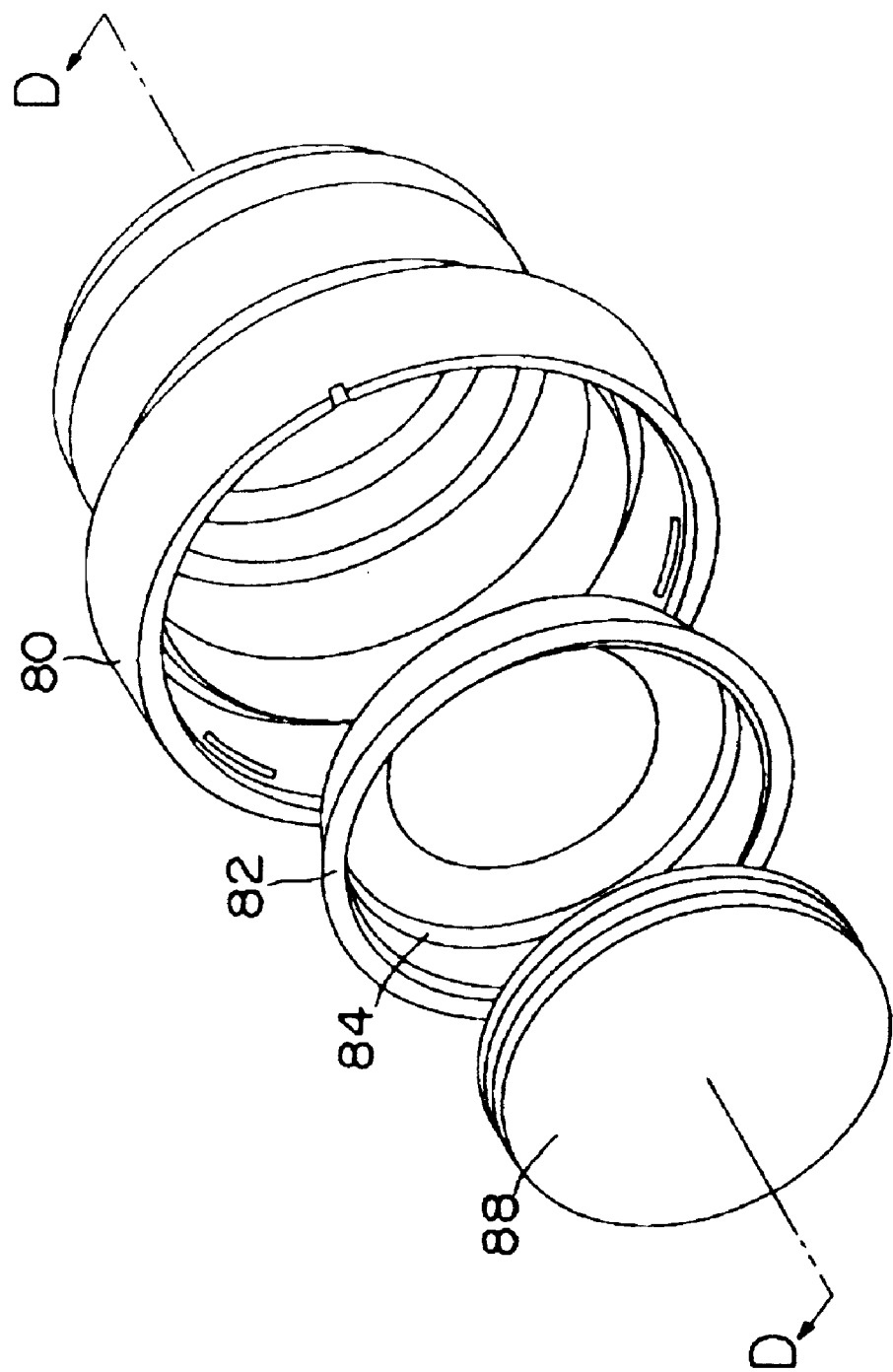
FIG. 7 is a perspective view of the blotter assembly.
Figure 10:
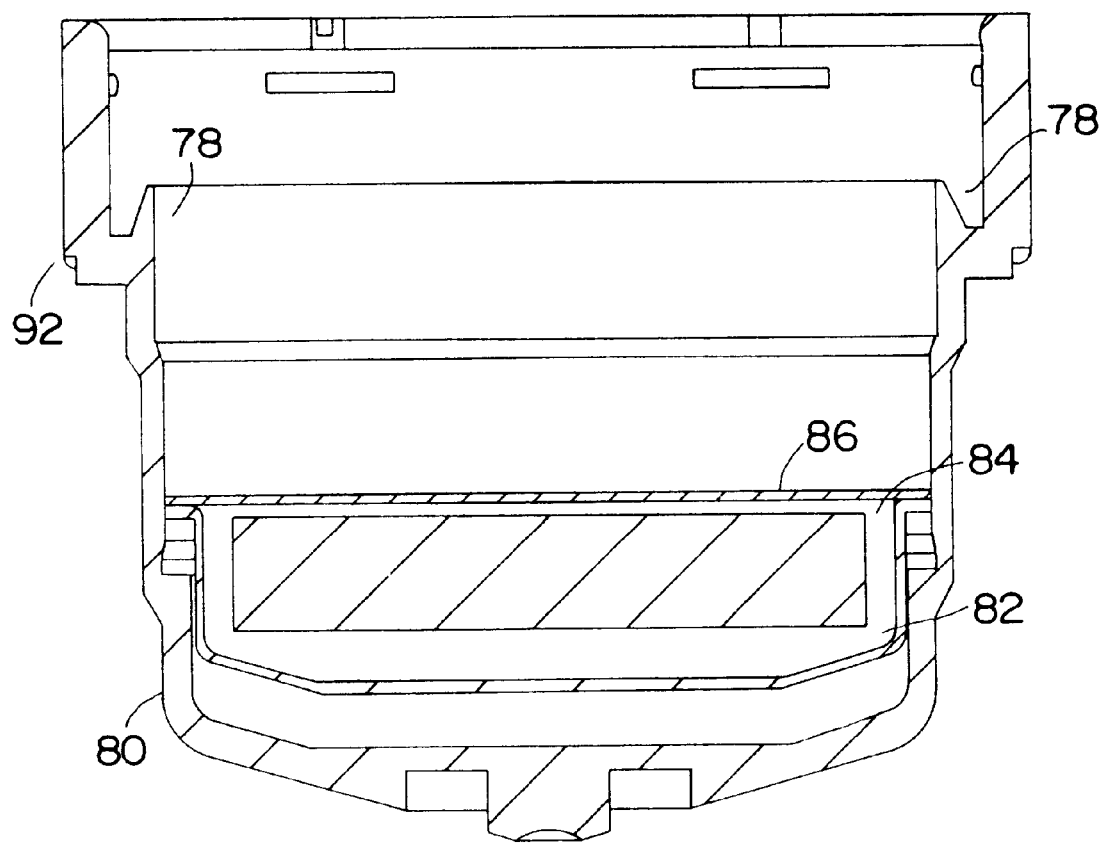
FIG. 10 is a cross-sectional view along the line D—D of the blotter sub-assembly shown in FIG. 7.
Figure 11:
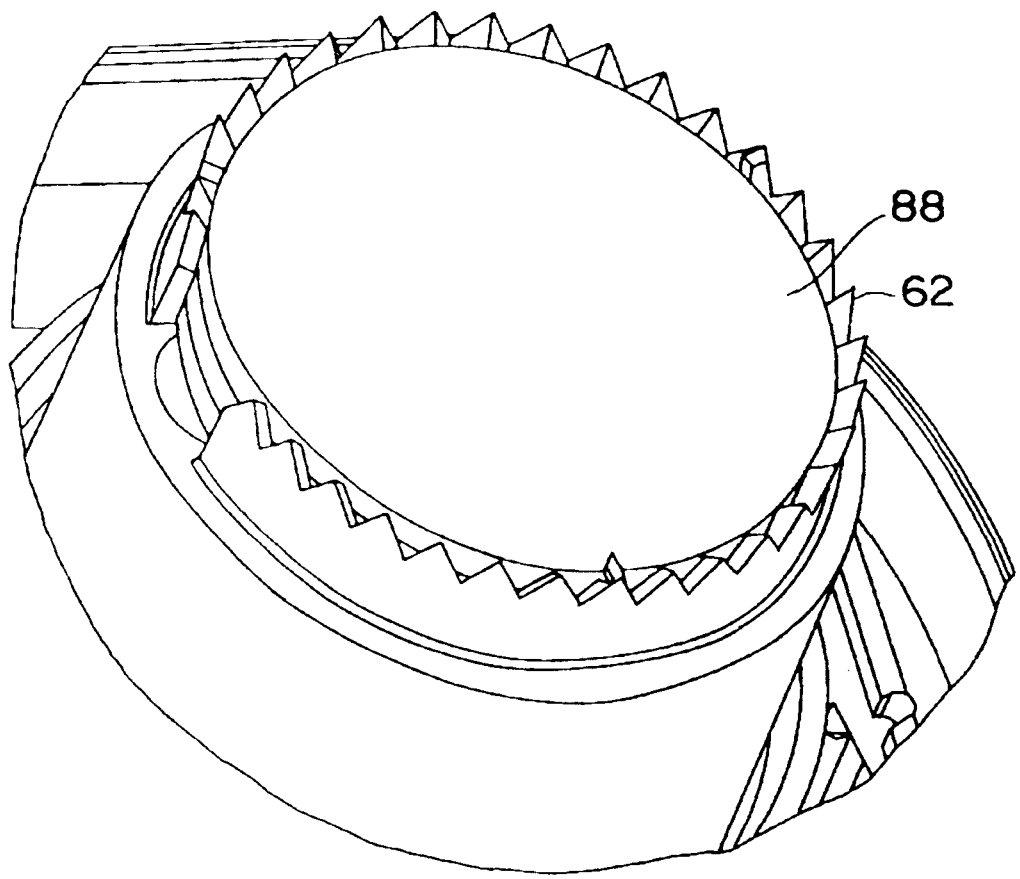
FIG. 11 is a perspective view of the blotter assembly as assembled on the sub-assembly shown in FIG. 8.

Cap 80 which can best be seen in FIGS. 7 and 10, defines a plurality of features. As seen in FIG. 10, cap 80 has a charge transfer medium reservoir 82 resident therein which also defines an aperture 84 across the top thereof, which is perforatably sealed with a rupturable seal or cover 86 placed across the aperture 84 aforementioned. Surmounting medium storage area 82 and perforatable seal 86 is a medium delivery apparatus 88 which in the preferred embodiment consists of a capillary active blotter assembly 88 which, upon perforation of the rupturable seal or cover 86, is operative to effect delivery of the charge transfer media from the reservoir or storage area 82 to the electrochemical cell housing 54 as shown in FIG. 11.

As aforementioned, extension 34 is adapted to allow cap 80 to assume a plurality of positions. In the first of these positions cap 80 is located outwardmost from extension 34. In this configuration the charge transfer medium is retained by rupturable seal 86 within reservoir 82.

Upon assembly of pump module 12 with syringe 14 and rotation to a first position corresponding to a first cam flat 22 engaged with indent 25, as aforementioned, the cup is placed into this initial position. Upon further rotation of syringe body 14 corresponding to a rotation of radial cam 20 the syringe advances up ramp 24 to engage flat 22 with lip 18 causing annular ramp 90 to impinge upon the exteriorally extensive cup ridge 92 thereby executing a linear motion of the cup 80 and driving the reservoir 82 and perforatable seal 86 into the toothed perforating member 60, and thereby releasing the charge transfer medium into the medium delivery apparatus 88 thereby transferring the medium to the electrochemical cell 54 coincident with electrical activation of the cell 54.

Situated in the pump module 12 and in fluid communication with the gas receiving chamber 110, a overpressure relief valve assembly 300 is operative to release gas generated by the electrochemical cell 54 and introduced into the gas receiving chamber 110.

Figure 13:
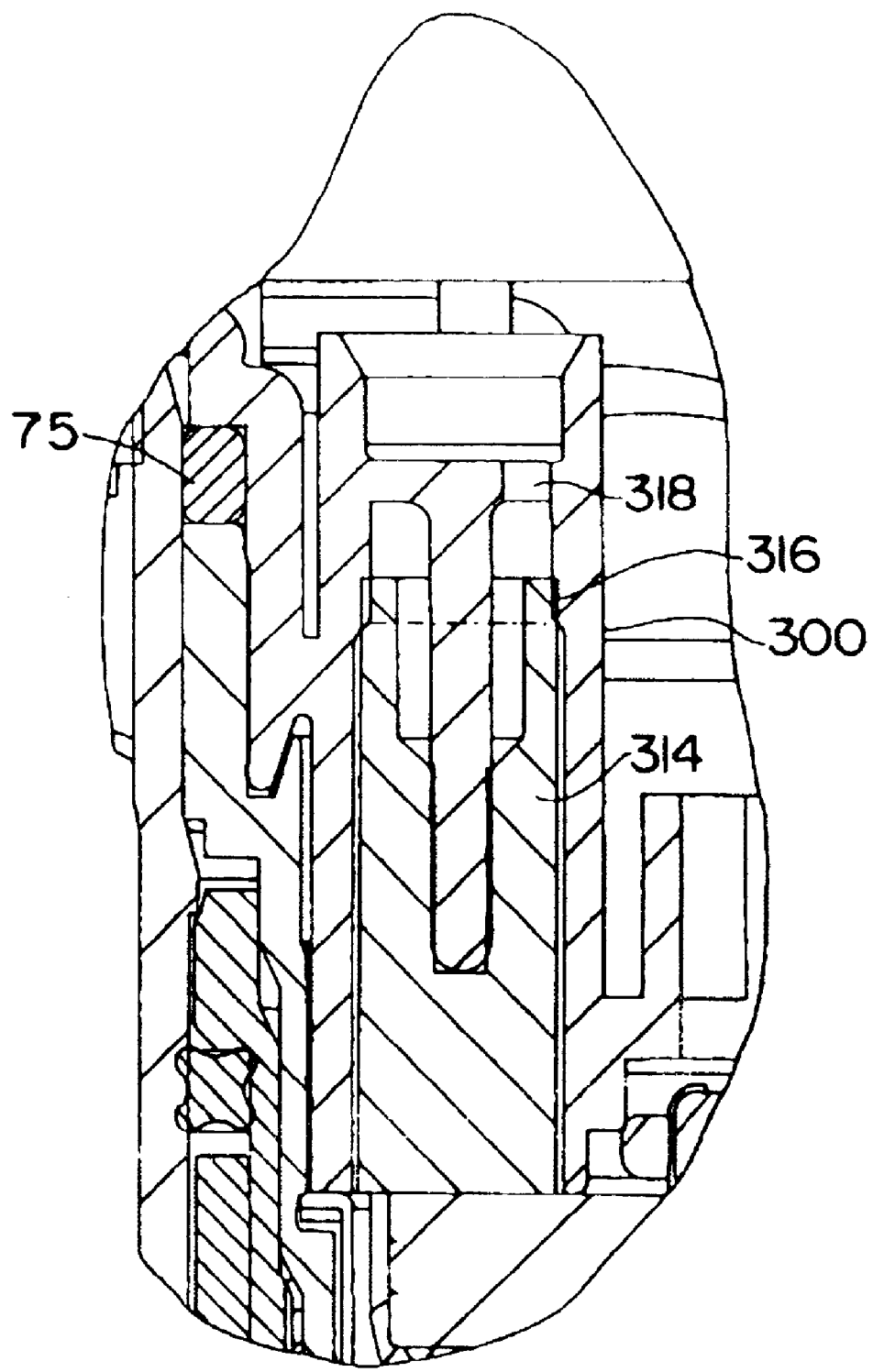
FIG. 13 is a cross-sectional view of the gas relief valve.

Should an occlusion or other interruption of the flow of medicament be experienced by the pump, an overpressure relief valve assembly, as shown in FIG. 13, is provided to allow reaction products to escape the syringe. The overpressure relief valve assembly 300 consists of a substantially cylindrical port 70 which is occluded by a elastomeric valving member 314 which is cooperative with valve seat 316 to provide for a fixed overpressure release. In operation the overpressure release valve 300 is acted upon by the presence of a pressurized atmosphere within the gas receiving chamber 110 wherein this atmosphere acts to provide a force against the elastomeric member 314 tending to displace the elastomeric valving member 314 from the valve seat 316. This displacement is counteracted by the elastic properties of the elastomeric valving member 314 to such an extent as to keep the elastomeric valving member 314 in contact with the valve seat 316 up to a specific predetermined pressure wherein the force supplied by the atmosphere resident in the gas chamber 110 is sufficient to move the elastomeric valving member 314 off of the valve seat 316 thereby allowing gas to escape through gas release ports 318 to the exterior of the pump module 12, at which time the elastic properties of the elastomeric valve member 314 will provide sufficient force to reset same against the valve seat 316 thereby closing off port 318 and allowing the gas receiving chamber to repressurize up to the final pressure prior to actuation of the overpressure relief valve 300.

Figure 3:
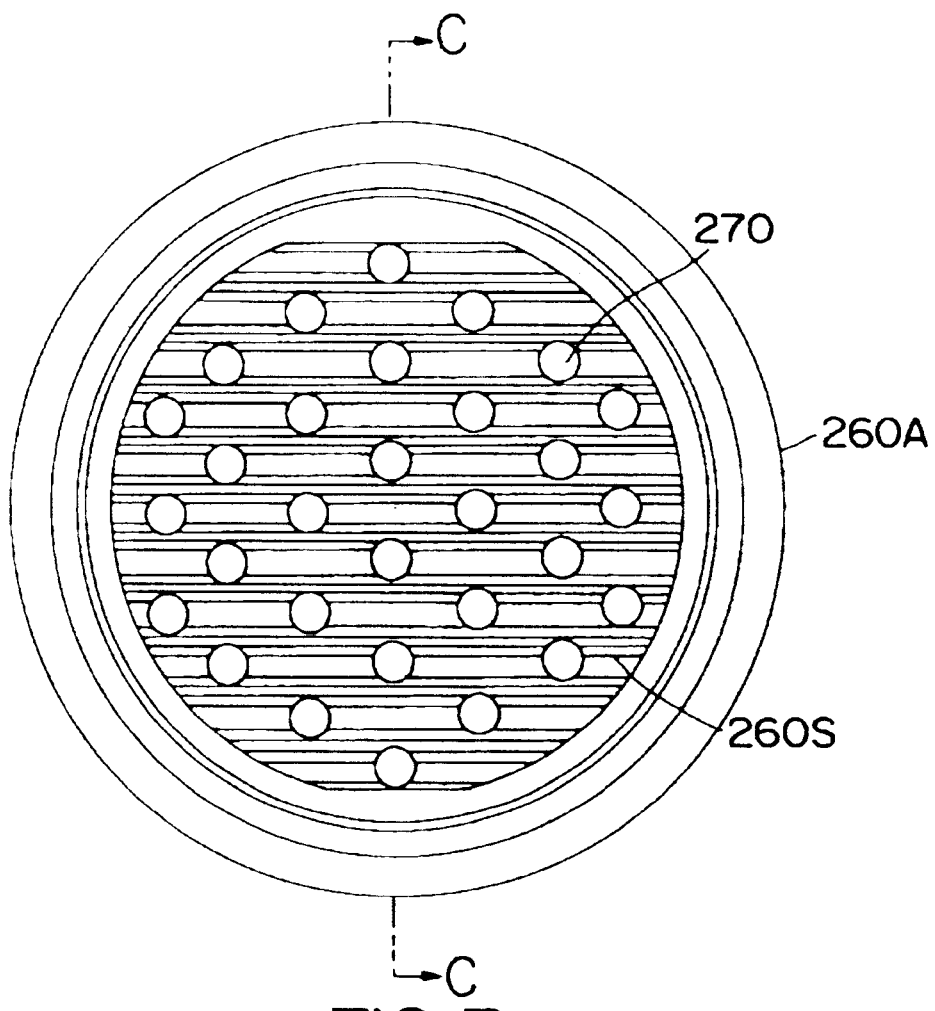
FIG. 3 is a plan view of the electrochemical cell assembly.
Figure 4:
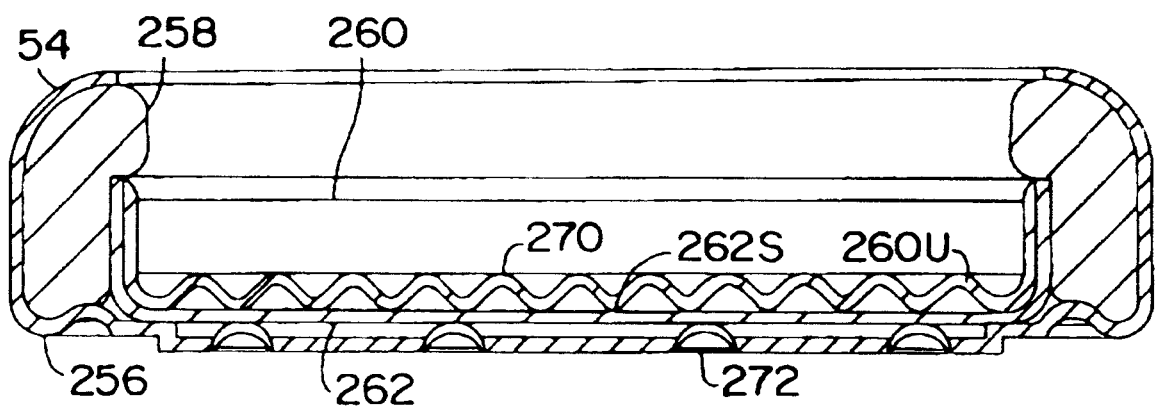
FIG. 4 is a cross-sectional view substantially along line C—C of FIG. 3.

The electrochemical cell assembly 54, as shown in FIGS. 3 and 4, consists of an anode body 256 which further includes the exterior of the assembly. Interior to the anode body 256 is an annular seal 258 wherein this annular electrochemical cell seal 258 resides conterminous with the interior dimension of the anode body 256. Interior to the seal 258 is a cathode body 260 which also structurally comprises the interior body of the assembly 54. Located conterminous with the cathode body 260 is the electrochemically active medium or membrane 262 which in the preferred embodiment is composed of Nafion as aforedescribed. The electrochemical membrane 262 is placed in contact with the cathode body and upon assembly the cathode body and electrochemical membrane are pressed past seal 258 so as to place the electrochemical membrane under tension due to frictional forces between the electrochemical membrane 262 and the seal 258 as the cathode body 260 and electrochemical membrane 262 are emplaced thereagainst. At this time seal 258 is already resident within the anode body 256 so as to provide a positive seat during assembly. Returnng now to the cathode body, as can be seen on the FIGS. 3 and 4, the central surface 260S of the cathode body 260 is uniaxially undulate. These undulations are placed as aforementioned along a first electrochemical cell axis 260A defined as being parallel to the longitudinal dimension of these undulations 260U. Placed therebelow, wherein the membrane is interstitial between the anode body 256 and cathode body 260, the anode body 256 further defines a second electrochemical cell axis which is defined as being parallel with the longitudinal extension of the undulations 260U impressed upon the anode body.

In the preferred embodiment the first electrochemical cell axis and the second electrochemical cell axis are at an angle to each other so as to provide a plurality of distributed electrical contact areas across the surface of the membrane 262. To allow feedstock to enter and reaction products to leave the surface of the membrane 262 a first plurality of holes 270 is defined upon the cathode body and a second plurality of holes 272 is defined upon the anode body wherein the first plurality of holes which are defined upon the cathode body 256 also known as cathode ports 270 and the second plurality of holes 272 defined on the anode body 256 which are also referred to as anode ports 272 are mutually disjoint so as to provide an even and uniform means for spiration of feedstock and reaction products to and from the membrane 262. An additional effect of the first and second undulate suffaces and the intersection therebetween across the membrane 262 is a marked reduction in the current gradient across the membrane surface wherein in the instant invention current is supplied across the membrane, and the undulate sufaces 260U, by providing a plurality of contact points, serves to minimize any variation in current supply through the membrane 262.

Figure 15:
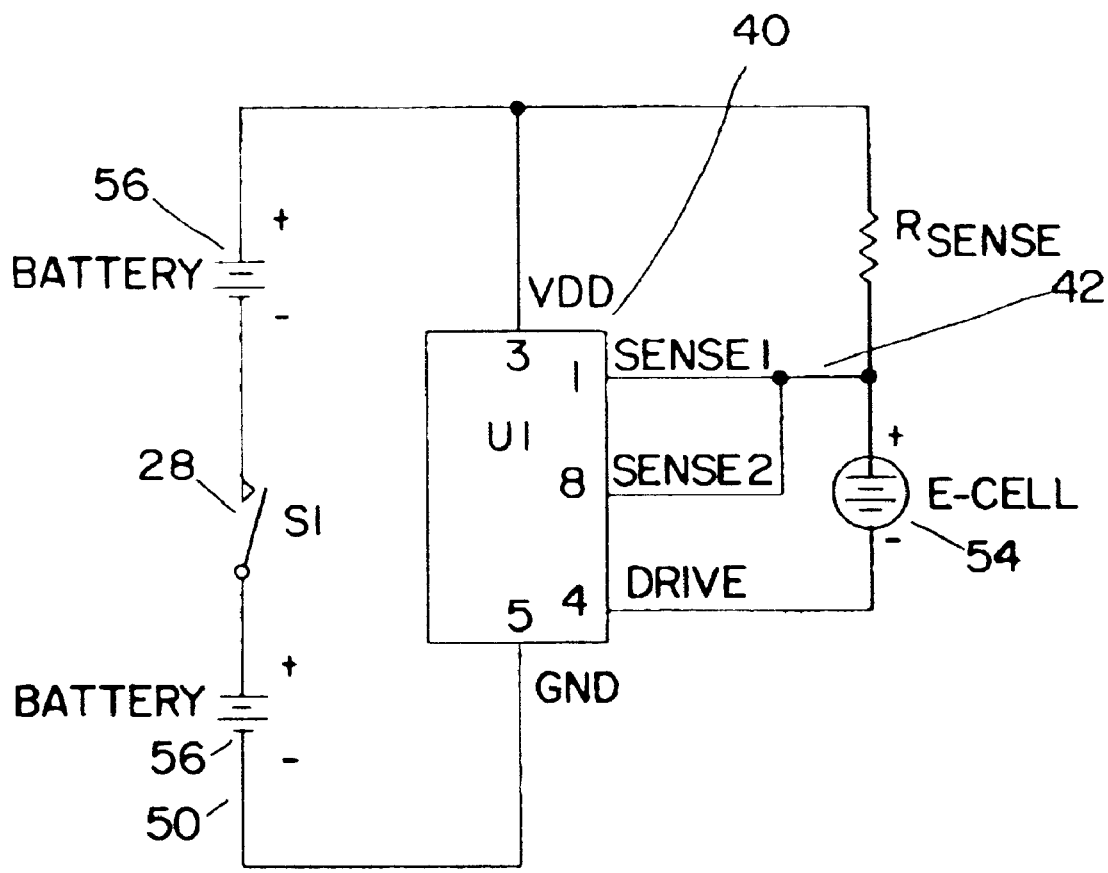
FIG. 15 is a schematic diagram of the control circuitry of the pump.

The electronic configuration of governing current control to the electrochemical cell 54 is depicted schematically in FIG. 15. A battery 56 supplies electrical power to the circuitry which is controlled by a current controlling chip which in the preferred embodiment is a Micronics Incorporated precision current controller type MX963 40 or a TPS 7101 manufactured by Texas Instruments Corp. Controller chip 40 is connected to a load resistor via the sense leads 42. These leads provide feedback for the controlling chip 40 to sense the amount of current passing through the electrochemical cell 54. The purpose of the resistor 46 is to provide a base current limiting to the sense portion of the integrated circuit 40 thereby determining the rate at which gas is generated by the electrochemical cell which is proportional to the rate of infusion. The output of current controlling chip 40 is thereafter connected to the electrochemical cell and returns to the battery via ground lead 50 thereby completing the circuit. Returning to switch 28, this switch corresponds to the reed switch aforedescribed.

This description of the presently preferred embodiment is indicative of the presently preferred configuration of the invention and is not to be construed to limit the scope of the invention to any extent greater than recited in the claims hereto appended.

In accordance with our invention, we claim:

1. An electrochemical syringe pump comprising:
    a syringe for delivering a supply of fluid;
    a plunger disposed within said syringe;
    a pump housing having an inner and outer surface, said inner surface is attached to said syringe, said pump housing comprises:
        an electrochemical cell;
        a power supply selectively connected to said electrochemical cell;
        a current control apparatus providing a limited current to said electrochemical cell from said power supply;
        a perforating member defined on said inner surface of said pump housing; and,
        a sealed charge transfer medium reservoir housed between said syringe and said pump housing wherein upon engagement of said perforating member with said sealed charge transfer medium reservoir, said perforating member perforates said sealed charge transfer medium reservoir and releases a charge transfer medium contained in said reservoir to contact said electrochemical cell to assist in a chemical reaction in said cell wherein said reaction causes an increase in pressure on said plunger to deliver a predetermined amount of said fluid.

2. The invention according to claim 1 wherein said syringe further comprising a barrel wherein said barrel has a draft angle defined thereon of substantially zero.

3. The invention according to claim 2 wherein a plunger adapted to slidingly fit within said barrel and a cruciform seal retained by said plunger.

4. The invention according to claim 3 wherein said cruciform seal in combination with said draft angle provides a substantially constant force of sliding friction therebetween.

5. The invention according to claim 1 wherein said current control controls a rate of infusion of medicament from said pump.

6. The invention according to claim 1 wherein said syringe further comprises a cam having a first position and a second position wherein said first position affixes said syringe to said pump while preventing activation of said cell.

7. The invention according to claim 6 wherein said second position activates said cell.

8. The invention according to claim 1 wherein said current control is a fixed resistive element which determines a rate of infusion by controlling a current available to said cell.

9. An electrochemically driven syringe pump for delivery of medicament to a patient; comprising a syringe for delivering a supply of medicament;
    a plunger disposed within said syringe;
    a pump head having an inner and outer surface wherein said inner surface is connected to said syringe;
    an electrochemical cell located within said pump head;
    a power supply and current control apparatus located within said pump head and selectively connected to said electrochemical cell;
    said pump further comprising a reservoir, in movable attachment to said pump head, which releasably retains a charge transfer medium, wherein said reservoir is covered by a perforatable membrane and said membrane is surmounted by a perforating member, extending from said inner surface of said pump head, which perforates said membrane when said pump is activated by attachment of said syringe to said pump head thereby releasing said charge transfer medium to come into contact with said electrochemical cell so as to assist said cell in executing an electrochemical reaction which increases pressure in said syringe to move said plunger and deliver a metered amount of medicament from said syringe.

10. The invention according to claim 9 wherein said reservoir further comprises a fluid retaining area and a blotter.

11. The invention according to claim 10 wherein said blotter contacts said electrochemical cell upon activation of said pump.

12. The invention according to claim 9 wherein said perforating member is a toothed annulus.

13. A gas driven syringe pump comprising a syringe and a plunger and a
    pump module housing an electrochemical cell;
    said pump module having a toothed perforating member extending therefrom;
    a cup-like fluid reservoir, slideably retained about said perforating member;
    a sealing member placed within said reservoir wherein said sealing member is emplaced between said perforating member and a charge transfer medium retained in said reservoir; wherein said perforating member perforates said sealing member upon activation of said pump by attachment of said pump module to said syringe wherein such attachment causes said syringe to slide said perforating member into said reservoir, thereby releasing said charge transfer medium from said reservoir to come into contact with said electrochemical cell retained within said pump module thereby assisting in an electrochemical reaction causing an increase in pressure in said syringe so as to move said plunger and deliver medicament from said syringe.

14. The invention according to claim 13 wherein said charge transfer medium being water.

15. The invention according to claim 14 wherein there is a said medium comprising a medium storage area and a medium delivery apparatus; said apparatus comprising a blotter to deliver said medium from said storage area to said electrochemical cell.

16. The invention according to claim 15 wherein said medium storage area further comprising a rupturable cover wherein said cover is adapted to be ruptured upon engagement with said pump module.

* * * * *